United States Patent
Tapper et al.

(10) Patent No.: US 11,904,178 B2
(45) Date of Patent: Feb. 20, 2024

(54) LIGHT THERAPY WEARABLE WITH JACKETED SIDE-EMITTING OPTICAL FIBER

(71) Applicant: Biothread LLC, Wayne, PA (US)

(72) Inventors: Jay Tapper, Wayne, PA (US); Daniel Bish, New York, NY (US); Daniel Shuter, New York, NY (US); Kristien Del Ferraro, Stamford, CT (US)

(73) Assignee: BIOTHREAD LLC, Bryn Mawr, PA (US)

( * ) Notice: Subject to any disclaimer, the term of this patent is extended or adjusted under 35 U.S.C. 154(b) by 190 days.

(21) Appl. No.: 17/680,527

(22) Filed: Feb. 25, 2022

(65) Prior Publication Data

US 2023/0271027 A1   Aug. 31, 2023

(51) Int. Cl.
*A61N 5/06* (2006.01)
*F21V 8/00* (2006.01)

(52) U.S. Cl.
CPC .......... *A61N 5/0613* (2013.01); *G02B 6/001* (2013.01); *A61N 2005/063* (2013.01); *A61N 2005/0645* (2013.01); *A61N 2005/0655* (2013.01); *A61N 2005/0659* (2013.01); *A61N 2005/0663* (2013.01)

(58) Field of Classification Search
CPC ................ A61N 5/06–2005/073; G02B 6/001
See application file for complete search history.

(56) References Cited

U.S. PATENT DOCUMENTS

| 4,234,907 A | 11/1980 | Daniel | |
|---|---|---|---|
| 2005/0237739 A1* | 10/2005 | Lee | A61N 5/0613 362/240 |
| 2013/0116612 A1 | 5/2013 | Stephan | |
| 2018/0369432 A1* | 12/2018 | Zaborsky | A61M 25/0097 |

FOREIGN PATENT DOCUMENTS

WO   WO-2022178109 A1 *  8/2022

OTHER PUBLICATIONS

Toray, Raytella Polymer Optical Fiber, available prior to Feb. 25, 2022, 14 pages.
Poly Optics Australia Pty. Ltd., Poly Optic Solid Core Fibre, May 7, 2003, 5 pages.

* cited by examiner

*Primary Examiner* — Jonathan T Kuo
(74) *Attorney, Agent, or Firm* — Rankin, Hill & Clark LLP

(57) ABSTRACT

A light therapy wearable includes a fabric panel and a side-emitting light tube affixed to or held against the fabric panel. The side-emitting optical light tube includes a side-emitting optical fiber and a jacket surrounding the side-emitting optical fiber. The side-emitting optical fiber includes a core and cladding surrounding the core. The core is made from a synthetic polymeric material. The jacket is made from a transparent or translucent material and has a durometer of at least 65 A and an outer diameter at least seven times a core diameter of the side-emitting optical fiber.

18 Claims, 5 Drawing Sheets

LIGHT THERAPY WEARABLE WITH JACKETED SIDE-EMITTING OPTICAL FIBER

BACKGROUND

Clinical studies have demonstrated the ergogenic and prophylactic benefits of red and infrared light therapy. Red and infrared light have been found to increase blood flow to muscles and joints, which can create an anti-inflammatory response, in addition to providing increased pliability. Muscle and joint stiffness as well as soreness have been demonstrated to be significantly reduced while muscle contractile function is simultaneously improved by using red and infrared light.

Clothing made from light emitting fabrics is described in U.S. Pat. No. 4,234,907. This patent, however, describes such clothing as a fad item or as safety clothing to emit light outward when the wearer wishes to be seen by others. US 2013/0116612 A1 discloses an illuminatable pad in FIG. 4 and different types of braces or supports in FIGS. 10-13. The pads, braces and supports disclosed in US 2013/0116612 A1 are described as including elongated polymeric tubes sold by Poly Optics Australia, Pty Ltd, which according to their literature have a gel core made from optically pure case acrylic monomers with a smallest available outer diameter (OD) for the core being 3.0 mm. Poly Optics Australia, Pty Ltd also sells the core placed in a jacket, which is described as a "Poly Jacket," and the smallest available OD when provided in the jacket according to the available literature is 5.0 mm.

There are problems that need to be overcome to provide a light therapy garment or wearable that incorporates side-emitting optical fibers. The literature available from manufacturers of side-emitting optical fibers warns against bending the fiber in a tight arc, and further warns against excessive force, repetitive bending and dropping. Also, when relatively larger optical fibers are used in wearables, as is the case in US 2013/0116612 A1, spacing between adjacent sections of the light tube must be increased to accommodate for the minimum bend radius of the optical fiber. There are also wearer comfort issues that result from the use of relatively larger optical fibers. US 2013/0116612 A1 attempts to overcome these comfort issues by changing the cross section of the optical fiber from a circular cross section to one that is more elliptical with tapered side edges (see FIGS. 14 and 14A in US 2013/0116612 A1). Also, US 2013/0116612 A1 describes placing the light tube in a foam to prevent discomfort for the user. These comfort and wearability problems, among others, need overcome to provide a consumer a light therapy wearable or garment that can be handled the same as or nearly the same as a typical garment that does not include side-emitting optical fibers.

SUMMARY

A light therapy wearable includes a fabric panel and a side-emitting light tube affixed to or held against the fabric panel. The side-emitting optical light tube includes a side-emitting optical fiber and a jacket at least partially surrounding the side-emitting optical fiber. The jacket is made from a light-transmissive material and has a durometer of at least 50 A and an outer diameter at least seven times a core diameter of the side-emitting optical fiber.

The side-emitting optical fiber can include a core made from a synthetic polymeric material. The side-emitting optical fiber can also include cladding surrounding the core. The synthetic polymeric material from which the core is made can be polymethyl methacrylate (PMMA).

The jacket can be made from silicone. The jacket can be extruded over the side-emitting optical fiber with the jacket surrounding and in contact with the side-emitting optical fiber. The side-emitting optical fiber can be movable with respect to the jacket in an axial direction, which is parallel with a longest dimension of the side-emitting light tube.

The core diameter of the side-emitting optical fiber can be less than or equal to 0.5 mm and at least 0.20 mm. The outer diameter of the jacket can be less than or equal to 2.4 mm. The outer diameter of the jacket can be less than 11.5 times the core diameter of the side-emitting optical fiber.

The light therapy wearable can further include a light-transmissive inner layer affixed to the fabric panel and at least partially covering the side-emitting light tube. The light therapy wearable can further include an intermediate channel layer between the fabric panel and the light-transmissive inner layer where the intermediate channel layer is affixed to the light-transmissive inner layer and defines a channel in which the side-emitting light tube is received. The light-transmissive inner layer can be a fabric mesh material. The intermediate channel layer can be a jersey cotton fabric sewn to the light-transmissive inner layer. The intermediate channel layer can also be jersey cotton bias tape that is adhered or sewn to the light-transmissive inner layer.

DETAILED DESCRIPTION

Figure 1:
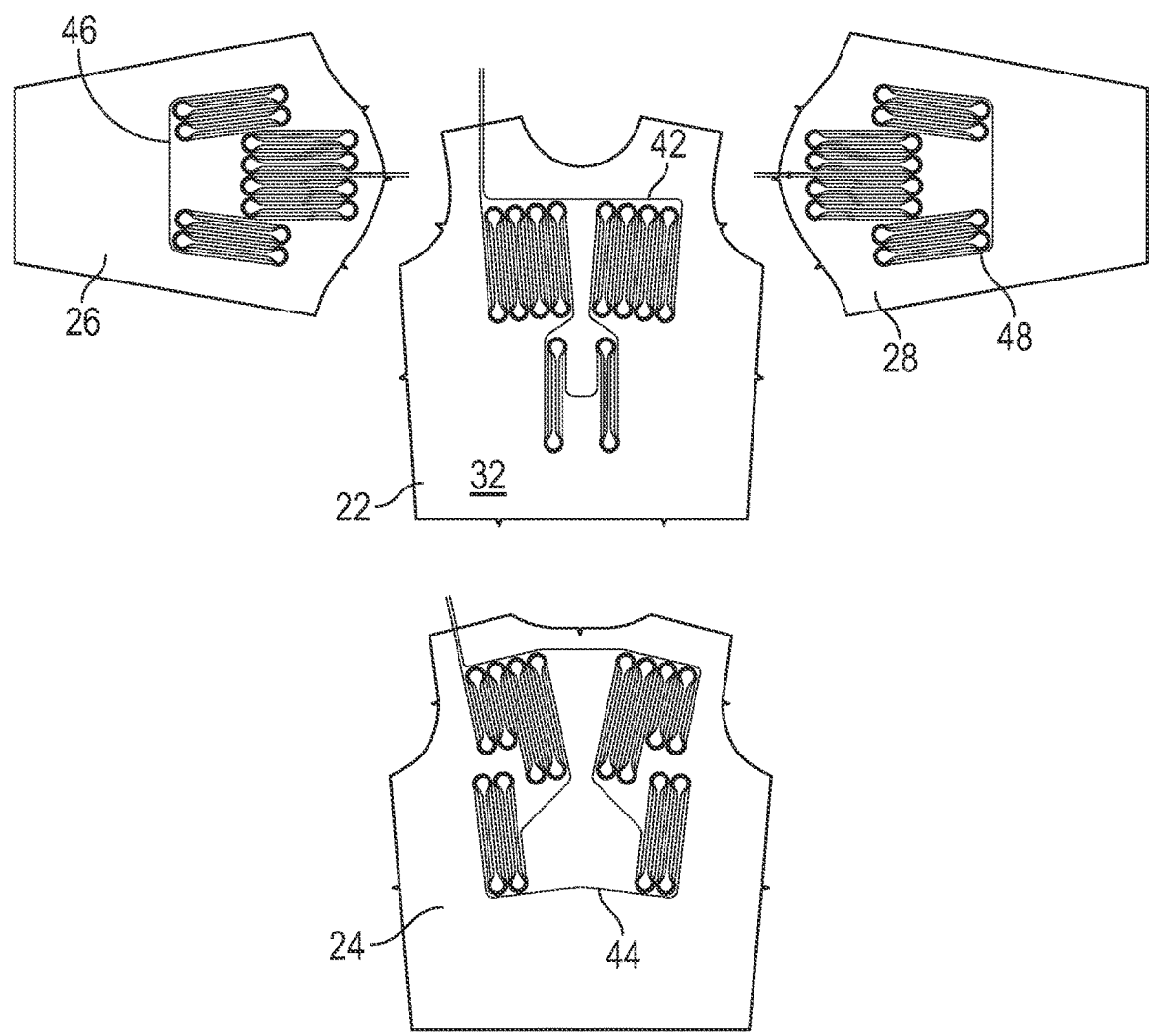
FIG. 1 is a plan view of panels laid flat and prior to being sewn together to make up a light therapy wearable.

With reference to FIG. 1, a therapeutic wearable, which is shown in the form of a shirt 20, is made up of a plurality of panels 22 (front), 24 (back), 26 (right sleeve), and 28 (left sleeve) that when sewn together make up the shirt 20. FIG. 1 depicts the panels 22-28 prior to being sewn together to form the shirt 20. FIG. 1 is a plan view showing an inner surface 32 (only shown for the front panel 22 in FIG. 1) of each panel, which is the surface facing the wearer when the shirt 20 is worn. The panels 22-28 can be either cut and sew pattern pieces or fully fashioned knitted structures. FIG. 1 depicts a shirt; however, other types of garments such as shorts, pants, gloves, a hat, socks, an undergarment, etc. could be manufactured in a similar manner. Once assembled, the garment is designed to be worn by a person in a similar manner as a conventional garment so that, for example, the shirt 20 shown in FIG. 1 would be worn over the upper body of a person.

The yarn from which each panel 22-28 is made can provide a comfort component for the shirt 20. Examples of such yarn can include cotton, polyester, cotton/polyester blends, microdenier polyester/cotton blends, and combinations thereof. The yarn can also include an elastic fiber such as lycra or spandex, and more than one type of yarn can form each panel. FIG. 1 depicts side-emitting light tubes 42, 44, 46, 48 affixed to the inner surface 32 of each panel 22, 24, 26, 28 respectively. Each side-emitting light tube 42-48 is optically connectable with at least one optical light source, which will be described in more detail below, and is configured to project light having a therapeutic wavelength toward a wearer of the shirt 20 after the shirt is assembled. A great or fewer number of panels and side-emitting light tubes could be employed to provide other light therapy wearables, e.g., wraps, braces, in addition to the shirt 20 depicted in FIG. 1 and other garments mentioned above while still employing the features described herein. Even though the shirt 20 with the side-emitting light tubes 42-48 will be described in detail below, the description is equally applicable to a wearable, e.g., a brace, an arm band, a leg band, and other garments including similar panels unless specifically mentioned otherwise.

Figure 2:
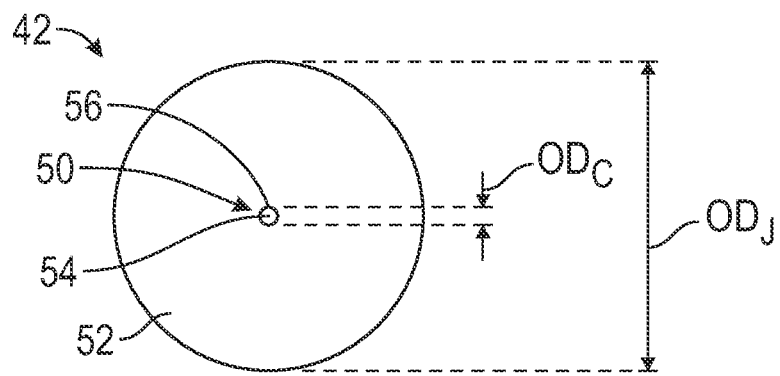
FIG. 2 is a cross-sectional view of a side-emitting light tube taken normal to a longest dimension of the side-emitting light tube.

FIG. 2 is a cross-sectional view of the side-emitting light tube 42. The other side-emitting light tubes 44, 46 and 48 have a similar construction. The side-emitting light tube 42 includes a side-emitting optical fiber 50 and a jacket 52 at least partially surrounding the side-emitting optical fiber 50. The side-emitting optical fiber 50 includes a core 54 and cladding 56 surrounding the core 54. The core 54 in the illustrated embodiment is made from a synthetic polymeric material, e.g., a high-purity polymethyl methacrylate (PMMA). The cladding 56 in the illustrated embodiment is made from a fluorinated polymer. The jacket 52 in the illustrated embodiment is made from silicone, which can be transparent or translucent, having a durometer of at least 50 A, and preferably at least 65 A. The jacket 52 can be extruded over the side-emitting optical fiber 50 such that the jacket 52 surrounds the side-emitting optical fiber 50 and is in contact with the cladding 56. Even though the jacket 52 is in contact with the cladding 56 so that no or a very small air gap is provided between them, the side-emitting optical fiber 50 is movable with respect to the jacket 52 in an axial direction, which is parallel with a longest dimension of the side-emitting light tube 42. Allowing for movement of the side-emitting optical fiber 50 with respect to the jacket 52 can be helpful in preventing damage to the side-emitting optical fiber 50 when the side-emitting light tube 42 is bent.

The side-emitting light tube 42 differs from conventional jacketed optical fibers by way of the material from which the jacket 52 is made and/or the cross-sectional area of the jacket 52 as compared to the cross-sectional area of the side-emitting optical fiber 50. The side-emitting optical fiber 50 can be purchased from Toray Industries, Inc. under the brand Toray Raytella side light plastic optical fiber as the "PS series." Similar optical fibers are available from other manufacturers. For example, Corning Incorporated also sells a light-diffusing optical fiber, which is made from a unique glass instead of a synthetic polymeric material. The Corning light-diffusing optical fiber has been jacketed in a PVC jacket. Literature available from Toray Industries describes jacket materials for optical fibers as either polyethylene (PE) or polyvinyl chloride (PVC). Literature available from Toray Industries also often describes multiple optical fibers in a single jacket. The jackets described in the available Toray Industries literature have an outer diameter (OD) that is only 2 to 2.5 times the OD of the optical fiber received in the jacket. In the available Toray Industries literature, there are also warnings against bending the fiber in a tight arc, and this literature recommends that the radius of the arc in which the fiber is bent should not be less than 20 times the OD of the optical fiber. This literature also warns against excessive force, repetitive bending and dropping.

With reference back to FIG. 2, the outer diameter ($OD_J$) of the jacket 52 is at least seven times the core diameter ($OD_C$) of the side-emitting optical fiber 50. As an example, the core diameter ($OD_C$) of the side-emitting optical fiber 50 can be an average of 0.24 mm (minimum 0.225 mm and maximum 0.255 mm) and the outer diameter ($OD_J$) of the jacket 52 between 1.75 mm and 2.4 mm. The side-emitting optical fiber 50 could have a smaller core diameter ($OD_C$). As another example, the core diameter ($OD_C$) of the side-emitting optical fiber 50 can be 0.5 mm with the outer diameter ($OD_J$) of the jacket 52 being between 7 times to 11.5 times greater than the core diameter ($OD_C$) of the side-emitting optical fiber 50. Having the core diameter ($OD_C$) of the side-emitting optical fiber 50 larger than 0.5 mm with the relatively larger jacket 52 can result in the side-emitting light tube 42 being too large in cross-section making it difficult to incorporate into the garment in an aesthetic and practically functional manner. Providing the jacket 52 with the outer diameter ($OD_J$) that is between 7 times to 11.5 times greater that the core diameter ($OD_C$) of the side-emitting optical fiber 50 protects the side-emitting optical fiber 50 against excessive force and dropping. It is also beneficial to inhibit bending the side-emitting optical fiber 50 in too tight of an arc, but the jacket 52 still allows needed flexibility to the side-emitting light tube 42 and is comfortable against the wearer's skin.

As mentioned above, there are difficulties with incorporating the side-emitting light tube 42 into a wearable or garment in an aesthetic and practically functional manner. If the side-emitting optical fiber 50 cannot withstand bending and forces that would be applied to the side-emitting optical fiber 50 during typical wear and handling of the wearable or garment, this would limit the practical functionality in that the wearable or garment would need to be handled much differently than a typical wearable or garment not having any side-emitting light tubes.

Figure 3:
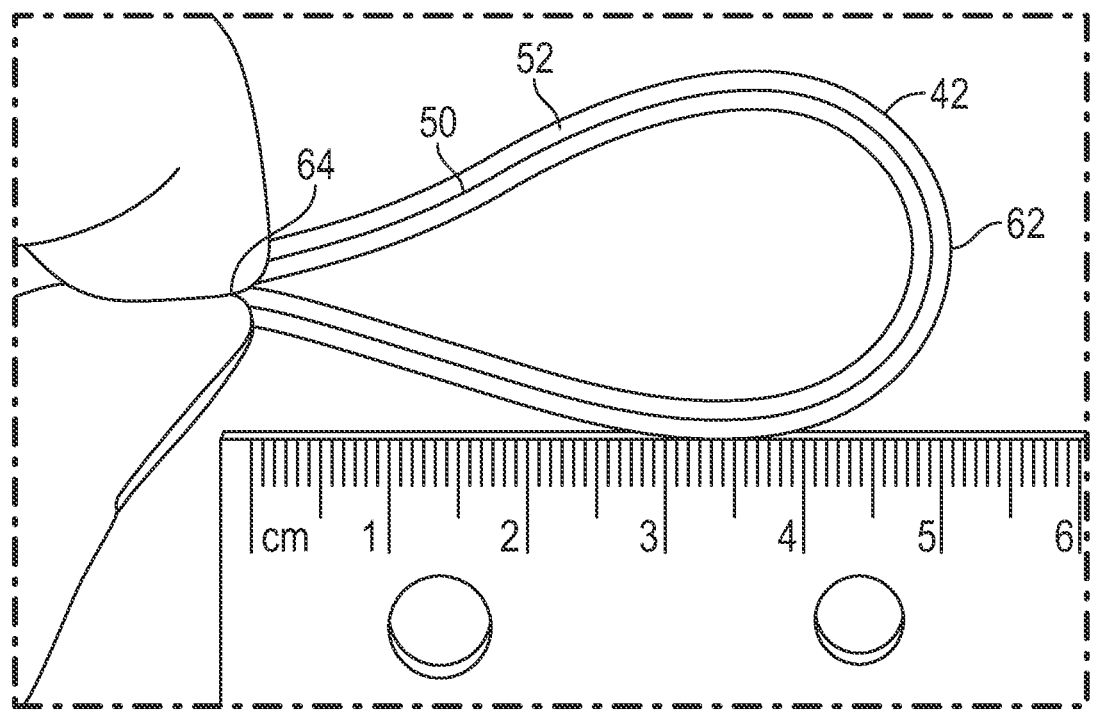
FIG. 3 depicts the side-emitting light tube folded over itself with no other external force being applied to the side-emitting light tube other than where the side-emitting light tube is being pinched.

FIG. 3 depicts the side-emitting light tube 42 folded over itself with no other external force being applied to the side-emitting light tube 42 other than where the side-emitting light tube 42 is being pinched. In FIG. 3, the side-emitting optical fiber 50 has a core diameter ($OD_C$) of 0.24 mm and the jacket 52 has an outer diameter ($OD_J$) 2.4 mm. The minimum bend radius for the side-emitting optical fiber 50 in FIG. 3 is about 12.5 mm, which is 50 times greater than the OD of the side-emitting optical fiber 50. When no jacket is provided on the side-emitting optical fiber 50 having a core diameter ($OD_C$) of 0.24 mm and side-emitting optical fiber 50 is pinched at a similar location, which is about 5 cm from a distal-most bend location 62 with respect to the pinch location 64, the side-emitting optical fiber 50 takes a very similar shape. When pinched to have a minimum bend radius that is 20 times greater than the core diameter ($OD_C$) of the side-emitting optical fiber 50, the side-emitting light tube 42 and the side-emitting optical fiber 50 without the jacket 52 take very similar shapes. From this one can conclude that the jacket 52 does not greatly limit the bending capability of the side-emitting optical fiber 50 when side-emitting optical fiber 50 maintains a bend radius greater than 20 times its core diameter ($OD_C$). Because the core diameter ($OD_C$) of the side-emitting optical fiber 50 is relatively small, for example as compared to the Poly Optics Australia, Pty Ltd polymeric tubes described in US 2013/0116612 A1, spacing between adjacent sections of the side-emitting light tube 42 (see FIG. 1) can be smaller than if a larger diameter side-emitting optical fiber was used. This smaller spacing between adjacent sections of the side-emitting light tube 42 allows for more light coverage on the wearer of the garment.

Figure 4:
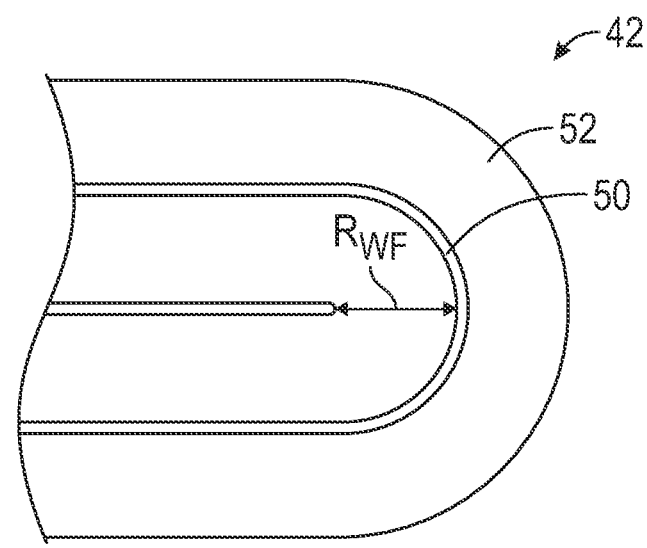
FIG. 4 is another side view of the side-emitting light tube folded over itself.

As mentioned above, available literature from Toray Industries recommends that the radius of the arc in which the side-emitting optical fiber 50 is bent should not be less than 20 times the core diameter ($OD_C$) of the side-emitting optical fiber 50; however, this radius is likely based on maintaining a desired performance for the side-emitting optical fiber 50 in its capacity to transmit light. There is another minimum radius of an arc in which the side-emitting optical fiber 50 is bent that will result in permanent mechanical damage, e.g., the side-emitting optical fiber 50 can break or crack so that light can no longer travel through the side-emitting optical fiber 50 at the location of the permanent mechanical damage. With reference to FIG. 4, the outer diameter ($OD_J$) of the jacket 52 is sized with respect to the core diameter ($OD_C$) of the side-emitting optical fiber 50 such that the minimum bend radius when folded ($R_{WF}$) for the side-emitting optical fiber 50 is greater than the minimum radius of the arc in which the side-emitting optical fiber 50 is bent that will result in permanent mechanical damage to the side-emitting optical fiber 50 with different external loads being applied to the side-emitting light tube 42. The minimum bend radius when folded ($R_{WF}$), which would occur when the side-emitting light tube 42 is folded over itself like that shown in FIG. 4, typically requires an external load nearer to the distal most bend location 62 than that shown in FIG. 3.

Figure 5:
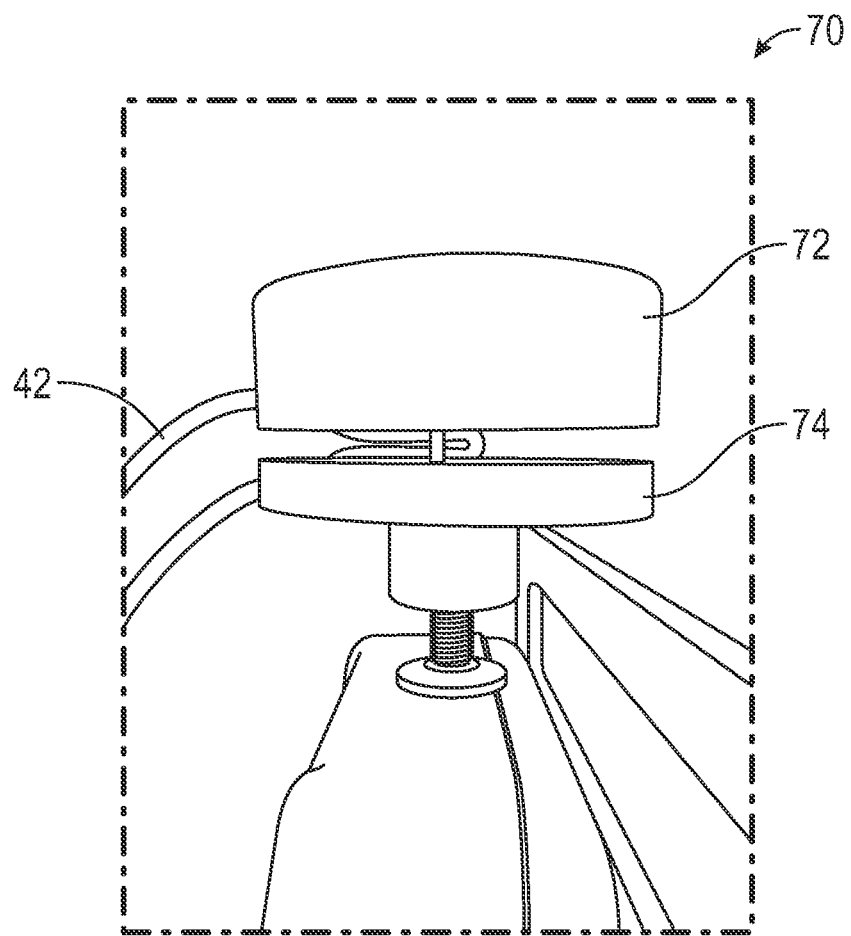
FIG. 5 schematically depicts a test jig for use with testing the side-emitting light tube.

To achieve the folded over configuration depicted in FIG. 4, an external force is applied to the side-emitting light tube 42 at a location closer to the distal-most bend location 62 as compared to the pinch location 64 depicted in FIG. 3. FIG. 5 schematically depicts a test jig 70 similar to one used to test the side-emitting light tube 42 including a 0.24 mm $OD_C$ PMMA core 54 and a jacket 52 made from silicone and having a durometer of about 65 A. Tests were performed with the jacket 52 having an $OD_J$ of 2.0 mm and an $OD_J$ of 2.4 mm. The test jig 70 includes an upper plate 72 and a lower plate 74 with the side-emitting light tube 42 folded over itself between the upper plate 72 and the lower plate 74. Before loading the side-emitting light tube 42 into the test jig 70, the side-emitting light tube 42 was cut to a set length. Both ends of the side-emitting light tube 42 were polished and a connector was attached to each end. One end of the side-emitting light tube 42 was optically connected with a laser. The other end of the side-emitting light tube 42 was optically connected to an optical power meter, which is a device that measures light output from a fiber end. With the laser turned on and directing light into the side-emitting light tube 42, the output from the end of the side-emitting light tube 42 was measured and recorded.

The side-emitting light tubes 42 were then loaded into the test jig 70 in the manner shown in FIG. 5, and an approximate 50 N force, via a 5 kg mass, was applied to the upper plate 72 so that each side-emitting light tube 42 was folded over in the configuration depicted in FIG. 4. After removal of the force, each side-emitting light tube 42 was then unfolded to a radius even much greater than that shown in FIG. 3 and tested for light loss by reconnecting the end of each side-emitting light tube 42 to the laser, directing light from the laser into each side-emitting light tube 42 and measuring the light output from the end of each side-emitting light tube 42 connected with the optical power meter.

After having applied the approximately 50 N force to each side-emitting light tube 42 while folded over itself, there was a 9% average light loss as compared to the previous measurement, which was taken before bending and applying the 50 N force, for the side-emitting light tube 42 with the 2.0 mm $OD_J$ jacket 52 and a 0% average light loss as compared to the previous measurement for the side-emitting light tube 42 with the 2.4 mm $OD_J$ jacket. Next, an approximate 100 N force, via a 10 kg mass, was applied to the upper plate 72 so that each side-emitting light tube 42 was folded over in the configuration depicted in FIG. 4. Each side-emitting light tube 42 was then similarly unfolded and tested for light loss. After having applied the 100 N force to each side-emitting light tube 42 while folded over itself, there was a 9% average light loss as compared to the previous measurement, i.e., after the 50 N force, for the side-emitting light tube 42 with the 2.0 mm $OD_J$ jacket 52 and a 2% average light loss as compared to the previous measurement for the side-emitting light tube 42 with the 2.4 mm $OD_J$ jacket 52. Next, an approximate 150 N force, via a 15 kg mass, was applied to the upper plate 72 so that the side-emitting light tube 42 was folded over in the configuration depicted in FIG. 4. The side-emitting light tube 42 was then similarly unfolded and tested for light loss. After having applied the 150 N force to the side-emitting light tube 42 while folded over itself, there was a 7% average light loss as compared to the previous measurement, i.e., after the 100 N force, for the side-emitting light tube 42 with the 2.0 mm $OD_J$ jacket 52 and a 2% average light loss as compared to the previous measurement for the side-emitting light tube 42 with the 2.4 mm $OD_J$ jacket 52. Next, an approximate 200 N force, via a 20 kg mass, was applied to the upper plate 72 so that each side-emitting light tube 42 was folded over in the configuration depicted in FIG. 4. Each side-emitting light tube 42 was then similarly unfolded and tested for light loss. After having applied the 200 N force to each side-emitting light tube 42 while folded over itself, there was an 8% average light loss as compared to the previous measurement, i.e., after the 150 N force, for the side-emitting light tube 42 with the 2.0 mm $OD_J$ jacket 52 and an 8% average light loss as compared to the previous measurement for the side-emitting light tube 42 with the 2.4 mm $OD_J$ jacket 52.

A similar test was performed using the Corning Incorporated light-diffusing optical fiber having the unique glass fiber jacketed in a PVC jacket. The glass fiber had an OD of 0.25 mm and the PVC jacket had an OD of 2.0 mm. A folded over configuration similar to the one shown in FIG. 4 with less than a 50 N force being applied to the PVC jacket was not able to be achieved without breaking the glass fiber.

The side-emitting light tube 42 with the 2.4 mm OM jacket 52 and the 0.24 mm $OD_C$ PMMA core 54 sustained significantly less light loss as compared to the side-emitting light tube 42 with the 2.0 mm $OD_J$ jacket 52 and the 0.24 mm $OD_C$ PMMA core 54 after forces were applied resulting in the side-emitting light tube 42 folding over itself. Not only was the $OD_J$ jacket 52 in relation to the $OD_C$ PMMA core 54 believed to be significant, but also the jacket 52 having a durometer of at least 65 A believed to play a role as well. The $OD_J$ jacket 52 is less than half the OD of the elongated polymeric tubes described in US 2013/0116612 A1, which can obviate the need to change cross-sectional shape of the side-emitting light tube 42 from circular as shown in FIG. 2 while still maintaining comfort when adjacent a wearer's skin. Furthermore, jacket 52 being made from a transparent or translucent silicone and having a durometer of at least 65 A with the $OD_J$ at least seven times the $OD_C$ of the side-emitting optical fiber 50 did not negatively impact the overall flexibility of the side-emitting light tube 42. As such, the relatively tight spacing between adjacent sections of the side-emitting light tube 42 as shown in FIG. 1 can be maintained.

The side-emitting light tube 42 is affixed to or held against the inner surface 32 of the panel 22 after the panel has been made, e.g., it is an additional step in the manufacturing process. For example, the side-emitting light tube 42 can be embroidered to the inner surface 32 of the panel 22 through the use of embroidery stitches (not shown). Alternatively, the side-emitting light tube 42 can be adhered to the inner surface 32 of the panel 22.

Figure 6:
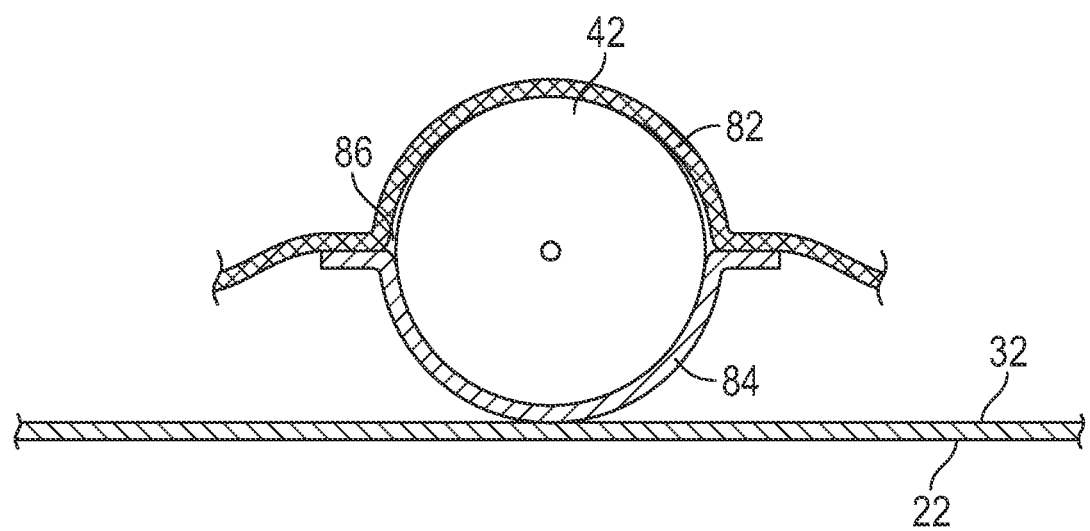
FIG. 6 is a cross-sectional view of the side-emitting light tube held against an inner surface of a panel.
Figure 7:
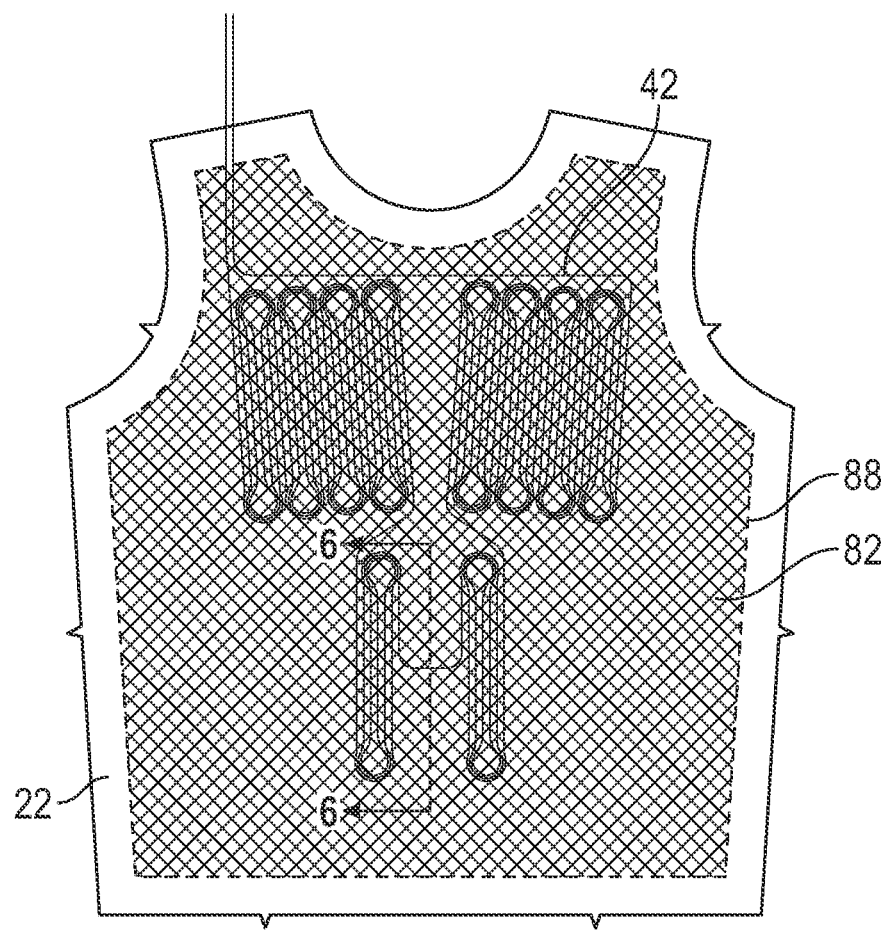
FIG. 7 is a plan view of a fabric panel having a light-transmissive inner layer affixed to the fabric panel and at least partially covering a side-emitting light tube.

In FIGS. 6 and 7, the side-emitting light tube 42 is shown held against the inner surface 32 of the front panel 22 by way of a light-transmissive inner layer 82 affixed to the front panel 22 and at least partially covering the side-emitting light tube 42. As seen in FIG. 6, an intermediate channel layer 84 is positioned between the front panel 22 and the light-transmissive inner layer 82. The intermediate channel layer 84 can be affixed to the light-transmissive inner layer 82 to define a channel 86 in which the side-emitting light tube 42 is received. In the embodiment illustrated in FIGS. 6 and 7, the light-transmissive inner layer 82 is a fabric mesh material. Examples of such fabric mesh material include sports mesh, power mesh, mesh netting, tulle, nylon mesh, and polyester mesh; however, other light-transmissive materials could be employed. The intermediate channel layer 84 can be any material composition such as cotton, polyester, spandex affixed to the light-transmissive inner layer 82. For example, the intermediate channel layer 84 can be a jersey cotton fabric sewn to the light-transmissive inner layer 82. Alternatively, the intermediate channel layer 84 can be a jersey cotton bias tape that is adhered, bonded or sewn to the light-transmissive inner layer 82. Affixing the intermediate channel layer 84 to the light-transmissive inner layer 82 instead of to the front panel 22 will not result in a seam noticeable on the exterior of the therapeutic wearable (shirt 20) allowing the therapeutic wearable to look from the exterior more similar to a typical garment that does not include side-emitting optical fibers. As mentioned above, the light-transmissive inner layer 82 can at least partially cover the side-emitting light tube 42 and/or the light-transmissive inner layer 82 can cover nearly the entirety of the inner surface 32 of the front panel 22. For example, the light-transmissive inner layer 82 can cover the entirety of the inner surface 32 within the area bounded by the broken line 88 shown in FIG. 7, which is provided to allow the front panel 22 to be sewn to other panels 24, 26 and 28 as well as to allow for hemming, which is typical in a conventional garment. Additionally, the light-transmissive inner layer 82 and the intermediate channel layer 84 can be employed with the other panels 24, 26 and 28 in a similar manner.

Figure 8:
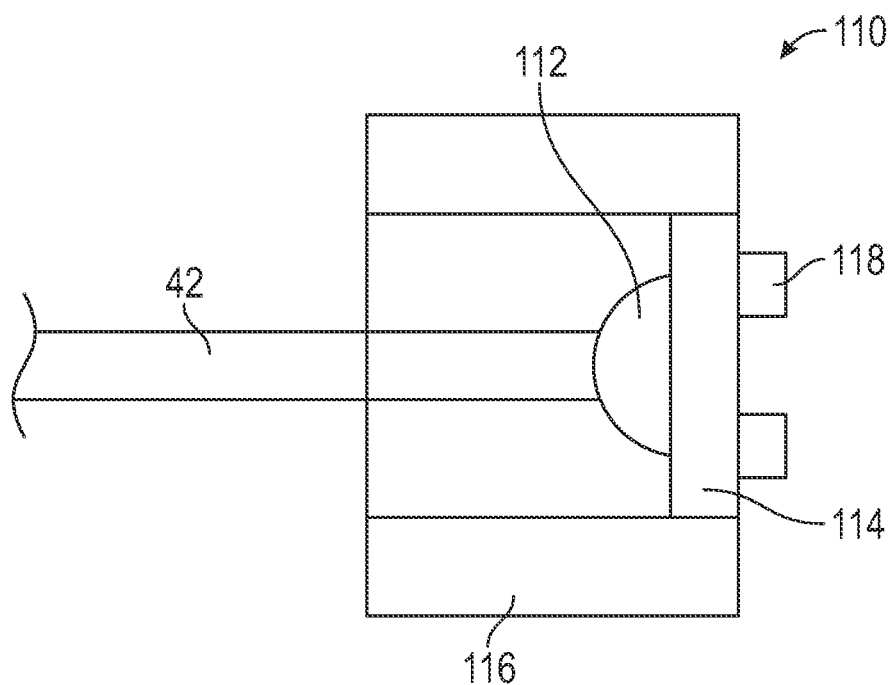
FIG. 8 is a schematic depiction of a light source assembly.

FIG. 8 is a schematic depiction of the light source assembly 110 in which a laser diode 112 is mounted to a circuit board 114, which are both received in a light assembly housing 116. Another type of light source, e.g., an LED, could be used instead of the laser diode 112. Also, the circuit board 114 need not be a rigid board, but could also be a flexible support with appropriate circuitry. Light source assembly side electrical contacts 118 extend from the circuit board 114 for receiving power.

Figure 9:
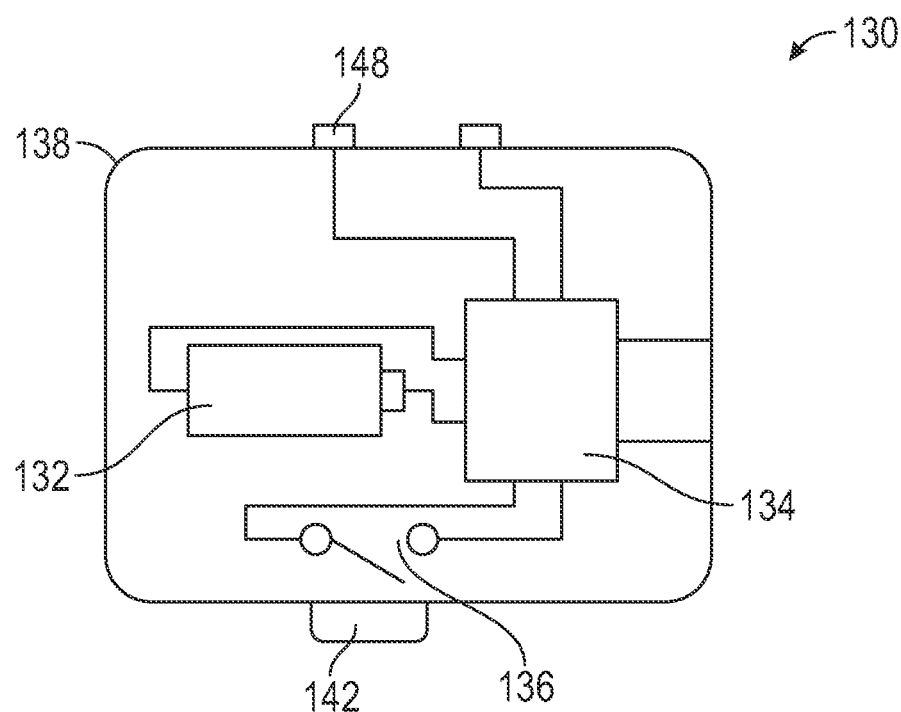
FIG. 9 is a schematic depiction of a power source assembly.

The light source assembly 110 cooperates with a power source assembly 130, which is schematically depicted in FIG. 9. The power source assembly 130 includes a battery 132 in electrical communication with a controller 134. The controller 134 can be an appropriate integrated circuit, for example. The controller 134 is in electrical communication with a switch 136 that can control power delivery to the light source assembly 110. The battery 132, the controller 134 and the switch 136 can be received in a power source housing 138, and an actuator 142, e.g., a button, can be accessible to a user on the outside of the power source housing 138 for operating the switch 136. Power supply contacts 148 on the power source assembly 130 are brought into in electrical communication with the light source assembly side electrical contacts 118 and with the switch 136 closed, power from the battery 132 can be supplied to the laser diode 112, which can direct light into the side-emitting light tube 42.

It will be appreciated that various of the above-disclosed embodiments and other features and functions, or alternatives or varieties thereof, may be desirably combined into many other different systems or applications. Also that various presently unforeseen or unanticipated alternatives, modifications, variations or improvements therein may be subsequently made by those skilled in the art which are also intended to be encompassed by the following claims.

The invention claimed is:

1. A light therapy wearable comprising:
   a fabric panel; and
   a side-emitting light tube affixed to or held against the fabric panel,
   the side-emitting light tube including a side-emitting optical fiber and a jacket at least partially surrounding the side-emitting optical fiber,
   the jacket being made from a light-transmissive material and having a durometer of at least 50 A and an outer diameter at least seven times a core diameter of the side-emitting optical fiber.

2. The light therapy wearable of claim 1, wherein the side-emitting optical fiber includes a core being made from a synthetic polymeric material.

3. The light therapy wearable of claim 2, wherein the side-emitting optical fiber includes cladding surrounding the core.

4. The light therapy wearable of claim 2, wherein the synthetic polymeric material from which the core is made is polymethyl methacrylate (PMMA).

5. The light therapy wearable of claim 1, wherein the jacket is made of silicone.

6. The light therapy wearable of claim 5, wherein the jacket is extruded over the side-emitting optical fiber with the jacket surrounding and in contact with the side-emitting optical fiber.

7. The light therapy wearable of claim 6, wherein the side-emitting optical fiber is movable with respect to the jacket in an axial direction, which is parallel with a longest dimension of the side-emitting light tube.

8. The light therapy wearable of claim 1, wherein the core diameter of the side-emitting optical fiber is less than or equal to 0.5 mm.

9. The light therapy wearable of claim 8, wherein the core diameter of the side-emitting optical fiber is at least 0.20 mm.

10. The light therapy wearable of claim 9, wherein the outer diameter of the jacket is less than or equal to 2.4 mm.

11. The light therapy wearable of claim 1, wherein the side-emitting optical fiber is movable with respect to the jacket in an axial direction, which is parallel with a longest dimension of the side-emitting light tube.

12. The light therapy wearable of claim 1, wherein the outer diameter of the jacket is less than 11.5 times the core diameter of the side-emitting optical fiber.

13. The light therapy wearable of claim 1, further comprising a light-transmissive inner layer affixed to the fabric panel and at least partially covering the side-emitting light tube.

14. The light therapy wearable of claim 13, further comprising an intermediate channel layer between the fabric panel and the light-transmissive inner layer, the intermediate channel layer being affixed to the light-transmissive inner layer and defining a channel in which the side-emitting light tube is received.

15. The light therapy wearable of claim 14, wherein the light-transmissive inner layer is a fabric mesh material.

16. The light therapy wearable of claim 15, wherein the intermediate channel layer is a jersey cotton fabric sewn to the light-transmissive inner layer.

17. The light therapy wearable of claim 15, wherein the intermediate channel layer is jersey cotton bias tape that is adhered or sewn to the light-transmissive inner layer.

18. The light therapy wearable of claim 14, wherein the intermediate channel layer is not affixed to the fabric panel.

\* \* \* \* \*